United States Patent [19]
Krstulovic

[11] Patent Number: 5,935,948
[45] Date of Patent: Aug. 10, 1999

[54] METHOD OF TREATING AND PREVENTING GALLSTONES

[76] Inventor: Veljko J. Krstulovic, 609 W. 114th St. Apt. 62, New York, N.Y. 10025

[21] Appl. No.: 09/056,655

[22] Filed: Apr. 7, 1998

Related U.S. Application Data

[60] Provisional application No. 60/043,133, Apr. 9, 1997.

[51] Int. Cl.⁶ .................................................. A61K 31/56
[52] U.S. Cl. ............................................................ 514/177
[58] Field of Search ............................................. 514/177

[56] References Cited

U.S. PATENT DOCUMENTS 3,882,248  5/1975  Igimi et al. .
4,793,948  12/1988  Hatono et al. .

OTHER PUBLICATIONS

Besancon et al. Therapie, 25 (3), 463–85 (France) [Abstract], 1970.
Teplick et al. American Journal of Roentgenology, 138 (2) 271–3 [Abstract], 1982.

*Primary Examiner*—Raymond Henley, III
*Attorney, Agent, or Firm*—Richard S. Clark; Lisa B. Kole

[57] ABSTRACT

The present invention relates to a method of treating and/or preventing gallstones comprising administering a therapeutically effective amount of dehydrocholic acid. It is based, at least in part, on the discovery that consistent usage of dehydrocholic acid resulted in the dissolution of gallstones and prevention, elimination and/or amelioration of biliary colic in four subjects.

10 Claims, No Drawings

METHOD OF TREATING AND PREVENTING GALLSTONES

This application claims benefit under 35 U.S.C. 119 (e) over Provisional Application No. 60/043,133 filed Apr. 9, 1997.

1. INTRODUCTION

The present invention relates to a method of preventing and/or treating gallstones, as well as elimination, amelioration, and/or prevention of biliary colic and diminishing or eliminating biliary colic comprising administering a therapeutic amount of dehydrocholic acid.

2. BACKGROUND OF THE INVENTION

2.1 Dehydrocholic Acid

Bile acids and their conjugates are essential components of bile. The physiological effects of bile acids as a whole include: induction of bile flow; feedback inhibition of bile acid synthesis; modulation of cholesterol synthesis; elimination of cholesterol (bile acids are water-soluble products of cholesterol metabolism and also solubilize cholesterol in bile and promote intestinal cholesterol excretion); and facilitation of dispersion and absorption of lipids and fat-soluble vitamins.

Bile acids increase the output of bile and hence are called choleretic drugs. Dehydrocholic acid (also known as 3,7, 12-Triketocholanic acid; Cholan DH; Decholin; Dehycol; Bilidren; Acolen; Cholagon; Chologon; Deidrocolico Vita; Didrojcolo; Hebile; Felacrinos; Dilabil; Bilostat; Oxycholin; and Procholon, Formula I, below), a semisinthetic cheolate, evokes the secretion of a bile of low specific gravity; it is therefore called a hydrocholeretic acid, which by thinning the bile facilitates its flow. The increase in bile flow evoked by bile acids is not a result of true cholepoiesis, since the augmented flow is only that necessary to secrete the increased load of bile acid imposed by that administered.

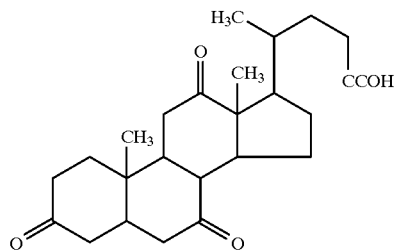

Dehydrocholic Acid

Naturally occurring bile acids, accounting for 95 percent of biliary bile acids, include cholic acid, chenodeoxycholic acid, and deoxycholic acid; minor bile acids include lithocholic acid and ursodeoxycholic acid. Glycine and taurine conjugates of bile acids, known as bile salts, readily form micelles with and emulsify lipids in conjunction with biliary phospholipids.

Some naturally occurring bile acids have been used therapeutically, by virtue of their ability to decrease the cholesterol content of bile, in the dissolution of cholesterol gallstones. Chenodeoxycholic acid at daily doses of 14–16 mg/kg of body weight, ursodeoxycholic acid at daily doses of 8–10 mg/kg of body weight, or a combination of 5–7 mg/kg of body weight per day of each, have been used for this purpose. Such administration may be associated with undesirable side effects, however, such as diarrhea and, in the case of chenodeoxycholic acid, elevated plasma transaminase activity and elevated serum cholesterol in the low-density lipoprotein (LDL) fraction.

Ursodeoxycholic acid (ursodiol; "ACTIGall"), at 8 to 10 mg/kg per day, is as effective as higher doses of chenodeoxycholic acid, causes diarrhea less frequently than chenodeoxycholic acid, and does not alter serum cholesterol or plasma transaminase activity. As a result of side effects, therapy with chenodeoxycholic acid alone is not recommended. However, combination therapy with lower doses of chenodeoxycholic acid and ursodeoxycholic acid (each at 5 to 7 mg/kg per day) achieves satisfactory results with fewer adverse effects. Administration of ursodeoxycholic acid alone remains the preferred therapy.

At a daily dose of 750 mg of chenodeoxycholic acid (the highest dose tested), there was confirmed complete dissolution of radiolucent gallstones in only 13% of patients during 2 years of treatment. The incidence of significant hepatotoxicity was 3% among patients who received 750 mg of chenodeoxycholic acid daily; biochemical abnormalities disappeared spontaneously in all of these patients after cessation of treatment. Diarrhea occurred in 40% of patients, but it was mild and never caused termination of treatment. The mean plasma cholesterol concentration was elevated slightly. Ursodeoxycholic acid may be more effective than chenodeoxycholic acid, and it appears to have much less tendency to cause hepatotoxicity or diarrhea. Studies indicate that gallstones will recur in a relatively high percentage of patients after cessation of treatment with bile acids.

The useful effects of exogenous bile acids result from their capacity to decrease the cholesterol content of the bile and promote dissolution of cholesterol gallstones. Of the physiological bile acids, chenodeoxycholic acid and ursodeoxycholic acid, but not cholic acid, are effective in this regard, although through somewhat different mechanisms.

Bile acids have effects on the intestine that are similar to those of other anionic surfactants and stimulant laxatives; they reduce net absorption of water and electrolytes and cause diarrhea if they escape ileal absorption. Dehydrocholic acid is considered safe and effective as an oral laxative when administered to adults in a dosage of 750 mg to 1.5 g daily in three doses. Dehydrocholate is also an effective hydrocholeretic in this dosage range.

2.2 Gallstones

The majority of gallstones are composed of cholesterol which has, in the absence of adequate amounts of bile salts, precipitated from the bile. It has been estimated that 15 million people in the United States have gallstones but are asymptomatic. Eventually, however, 15 to 50 percent of these persons may be expected to develop the symptoms of gallbladder disease, most typically pain (Fishman et al., 1985, *Medicine*, Second Edition, J.P. Lippincott Co., Philadelphia). If a gallstone obstructs the cystic duct or, even more seriously, the common bile duct, the obstruction of bile flow (and the swollen gallbladder which results) results in severe pain and may constitute a surgical emergency. (Id.)

3. SUMMARY OF THE INVENTION

The present invention relates to a method of treating and/or preventing gallstones comprising administering a therapeutically effective amount of dehydrocholic acid. It is based, at least in part, on the discovery that consistent usage of dehydrocholic acid resulted in the dissolution of gallstones and prevention, elimination and/or amelioration of biliary colic in four subjects.

4. DETAILED DESCRIPTION OF THE INVENTION

The present invention relates to a method of treating and/or preventing gallstones comprising administering, to a subject in need of such treatment, a therapeutically effective amount of dehydrocholic acid.

The term "treating and/or preventing gallstones" is defined, herein, as substantially decreasing the size and/or number of gallstones present in a subject, or diminishing or eliminating the symptom of biliary colic in a subject. The foregoing may be monitored purely symptomatically, or by sonography, or by radiographic techniques, such as by X-ray, CAT scan, or MRI.

Dehydrocholic acid may be preferably administered orally to the subject. The usual daily dose of dehydrocholic acid may be 250–750 mg per day; larger doses do not appear to be necessary and may cause diarrhea. In specific, non-limiting embodiments, dehydrocholic acid may be administered in doses of 250 mg ingested once or twice per day, usually before meals or, for persons with sensitive gastrointestinal tracts, 125 mg two or three times per day before meals. In preferred specific nonlimiting embodiments, dehydrocholic acid may be administered in tablets of 150 mg ingested two or three times per day.

The foregoing doses may be accompanied by a laxative effect and/or gastrointestinal cramps.

5. EXAMPLE

Dissolution of Gallstones and/or Prevention of Biliary Colic in Four Subjects Patient number 1 was a 40 year old female suffering from biliary colic following fatty meals. She had a family history of gallstones, although she did not herself have detectable gallstones on presentation. In this patient, the administration of dehydrocholic acid was found to prevent biliary colic if taken before meals, and would ameliorate biliary colic post-prandially. She had been medicated with dehydrocholic acid for thirty years with no side effects noticed.

Patient number 2 was a 70 year old female with a history of cardiac disease who presented with biliary colic. Examination revealed numerous small gallstones in the patient's gall bladder. In view of the patient's cardiac disease history, she was considered to be a poor surgical candidate, and medical treatment with dehydrocholic acid was administered. The patient tolerated the medication well and had no recurrence of biliary colic. Periodic testing showed that the number of gallstones decreased until, four years after treatment had been initiated, a gall bladder series revealed no evidence of gallstones. This patient continued to take dehydrocholic acid until her death.

Patient number 3 was a 68 year old female who presented with severe discomfort in the gall bladder area and an ultrasound study which revealed the presence of gallstones. Being very apprehensive of a surgical procedure, the patient refused even laparoscopic cholecystectomy. Therapy with dehydrocholic acid was initiated, and gall bladder attacks ceased to recur. A sonographic study, performed four years after dehydrocholic acid therapy was initiated, indicated that the patient's gallstones had disappeared.

Patient number 4 was a 57 year-old female presenting with severe biliary colic for which she was hospitalized in 1993. Before that she suffered from frequent epigastric pain and discomfort. Gallstones were documented by sonographic study. The patient was sensitive to dehydrocholic acid and was taking only 125 mg twice a day. After 3½ years, her gallstones were still present, but during dehydrocholic acid therapy she was completely free of biliary pain. She continued to take dehydrocholic acid as long as it was available on the market.

The foregoing clinical data indicates that dehydrocholic acid is useful in the dissolution of gallstones and/or relief of biliary colic. A further advantage of deoxycholic acid therapy is the generally inocuous nature of the drug, where a mild laxative effect, with possible gastrointestinal cramping, are the only known side effects.

None of four treated patients had any biliary colic while taking dechol in. Patient No. 1 had been taking decholic for more than thirty years.

I claim:

1. A method of ameliorating biliary colic in a subject in need of such treatment, comprising administering to the subject, an effective amount of dehydrocholic acid.

2. The method of claim 1, wherein the amount of dehydrocholic acid and administered per day is 250–750 mg.

3. The method of claim 1, wherein the dose of dehydrocholic acid is 250 mg administered twice daily.

4. The method of claim 1, wherein the dose of dehydrocholic acid is 150 mg administered twice daily.

5. The method of claim 1, wherein the dose of dehydrocholic acid is 150 mg administered three times daily.

6. A method of preventing gallstone formation in a subject in need of such treatment comprising administering to the subject, an effective amount of dehydrocholic acid.

7. The method of claim 6, wherein the amount of dehydrocholic acid administered per day is 250–750 mg.

8. The method of claim 6, wherein the dose of dehydrocholic acid is 250 mg administered twice daily.

9. The method of claim 6, wherein the dose of dehydrocholic acid is 150 mg administered twice daily.

10. The method of claim 6, wherein the dose of dehydrocholic acid is 150 mg administered three times daily.

* * * * *